(12) United States Patent
Van De Wijdeven

(10) Patent No.: US 8,486,439 B2
(45) Date of Patent: *Jul. 16, 2013

(54) PARENTERAL FORMULATION

(75) Inventor: Gijsbertus Gerardus Petrus Van De Wijdeven, Maastricht (NL)

(73) Assignee: Bioneedle Technologies Group B.V., Eindhoven (NL)

( * ) Notice: Subject to any disclaimer, the term of this patent is extended or adjusted under 35 U.S.C. 154(b) by 670 days.

This patent is subject to a terminal disclaimer.

(21) Appl. No.: 12/529,525

(22) PCT Filed: Feb. 29, 2008

(86) PCT No.: PCT/NL2008/050121
§ 371 (c)(1), (2), (4) Date: Sep. 1, 2009

(87) PCT Pub. No.: WO2008/105663
PCT Pub. Date: Sep. 4, 2008

(65) Prior Publication Data
US 2010/0080839 A1    Apr. 1, 2010

Related U.S. Application Data

(60) Provisional application No. 60/892,401, filed on Mar. 1, 2007.

(30) Foreign Application Priority Data

Mar. 1, 2007 (EP) .................................. 07103348

(51) Int. Cl.
- *A61F 2/00* (2006.01)
- *A61K 47/00* (2006.01)
- *B29C 45/00* (2006.01)
- *B29C 47/00* (2006.01)

(52) U.S. Cl.
USPC ..................... 424/426; 514/778; 264/328.1

(58) Field of Classification Search
None
See application file for complete search history.

(56) References Cited

U.S. PATENT DOCUMENTS

| | | | |
|---|---|---|---|
| 2,668,162 A | 3/1952 | Lowe | |
| 2,703,316 A | 3/1955 | Schneider | |
| 3,616,758 A | 11/1971 | Komarov | |
| 3,636,956 A | 1/1972 | Schneider | |
| 3,839,297 A | 10/1974 | Wasserman et al. | |
| 3,948,263 A | 4/1976 | Drake, Jr. et al. | |
| 3,982,536 A | 9/1976 | Krogseng et al. | |
| 4,137,921 A | 2/1979 | Okuzumi et al. | |
| 4,157,437 A | 6/1979 | Okuzumi et al. | |
| 4,243,775 A | 1/1981 | Rosensaft et al. | |
| 4,326,524 A | 4/1982 | Drake et al. | |
| 4,443,430 A | 4/1984 | Mattei et al. | |
| 4,449,982 A | 5/1984 | Gould, III | |
| 4,664,664 A | 5/1987 | Drake, Jr. | |
| 4,673,438 A | 6/1987 | Wittwer et al. | |
| 4,975,479 A | 12/1990 | Satake et al. | |
| 5,076,983 A | 12/1991 | Loomis et al. | |
| 5,310,865 A | 5/1994 | Enomoto et al. | |
| 5,382,611 A | 1/1995 | Stepto et al. | |
| 5,409,973 A | 4/1995 | Bastioli et al. | |
| 5,439,953 A | 8/1995 | Ritter et al. | |
| 5,549,560 A | 8/1996 | Van De Wijdeven | |
| 5,736,209 A * | 4/1998 | Andersen et al. ............ | 428/36.4 |
| 5,989,214 A | 11/1999 | Van De Wijdeven | |
| 6,001,385 A | 12/1999 | Van De Wijdeven | |
| 6,025,458 A | 2/2000 | Lipinsky et al. | |
| 6,375,971 B1 | 4/2002 | Hansen | |
| 6,811,792 B2 | 11/2004 | Roser et al. | |
| 6,821,538 B2 | 11/2004 | Axelrod et al. | |
| 2006/0121083 A1 | 6/2006 | Mor | |

FOREIGN PATENT DOCUMENTS

| | | |
|---|---|---|
| EP | 0 118 240 A2 | 9/1984 |
| EP | 0326517 B1 | 1/1989 |
| EP | 0298920 B1 | 12/1992 |
| EP | 0282451 B1 | 6/1994 |
| EP | 0474705 B1 | 8/1995 |

(Continued)

OTHER PUBLICATIONS

Zobel, H.F. Molecules to Granules: A comprehensive starch review. Starch, 1988, vol. 40, pp. 44-50.*
L.S. Lai et al., Physichemical Changes and Rheological Properties of Starch during Extrusion (A Review), Biotechnol. Prog. 1991, 7 pp. 251-266.
R.F. Tester et al., "Hydrolysis of native starches with amylases", Science Direct, 130, (2006), pp. 39-54.
Daniel J. Gallant et al., "Microscopy of starch: evidence of a new level of granule organization", Carbohydrate Polymers, 32, (1997), pp. 177-191.
Van de Wijdeven, "Development and assessment of mini projectiles as drug carriers", Journal of Controlled Release, 85 (2002), pp. 145-162.

(Continued)

*Primary Examiner* — Susan Tran
*Assistant Examiner* — Jessica Worsham
(74) *Attorney, Agent, or Firm* — Gilberto M. Villacorta; Sunit Talapatra; Foley & Lardner LLP

(57) ABSTRACT

The present invention relates to a kinetic implant comprising (a) biodegradable material comprising opened starch, destructurized starch or a mixture of opened starch and destructurized starch, (b) a biologically or pharmaceutically active substance; and (c) a stabilizing component stabilizing the biologically or pharmaceutically active substance. The biodegradable material comprises about 50 to about 100 wt. % of opened starch, destructurized starch or a mixture of opened starch, based on the total weight of the biodegradable material, the biodegradable material having a bulk density of 1.0 to 1.5 kg/dm$^3$. The kinetic implant has a length :diameter ratio of more than 4, provided that the length of the kinetic implant is between 1 mm to 50 mm. The kinetic implant has a weight such that it can be provided with an amount of kinetic energy in the range of 0.1 to 10 J.

26 Claims, 1 Drawing Sheet

FOREIGN PATENT DOCUMENTS

| | | |
|---|---|---|
| EP | 0495056 B1 | 12/1995 |
| EP | 0118240 B2 | 6/1997 |
| EP | 0994564 A1 | 4/2000 |
| EP | 1 035 163 A2 | 9/2000 |
| EP | 0304401 B2 | 11/2000 |
| EP | 774975 B1 * | 3/2003 |
| EP | 0774975 B1 | 3/2003 |
| GB | 2190093 A | 11/1987 |
| WO | WO 87/06129 A1 | 10/1987 |
| WO | WO 90/11756 A1 | 10/1990 |
| WO | WO 92/15285 | 9/1992 |

OTHER PUBLICATIONS

Kirk-Othmer, "Starch", Encyclopedia of Chemical Technology, Silicon Compounds to Succinic Acid and Succinic Anhydride; Fourth Edition, (1997) vol. 22, pp. 699-719.

Elsevier Science Ltd "Modification of Starch Properties with Plasticizers" Trends in Polymer Science, vol. 4 (1996), pp. 128-132.

International Search Report corresponding to PCT/NL2008/050121, dated Aug. 5, 2008, 4 pages.

* cited by examiner

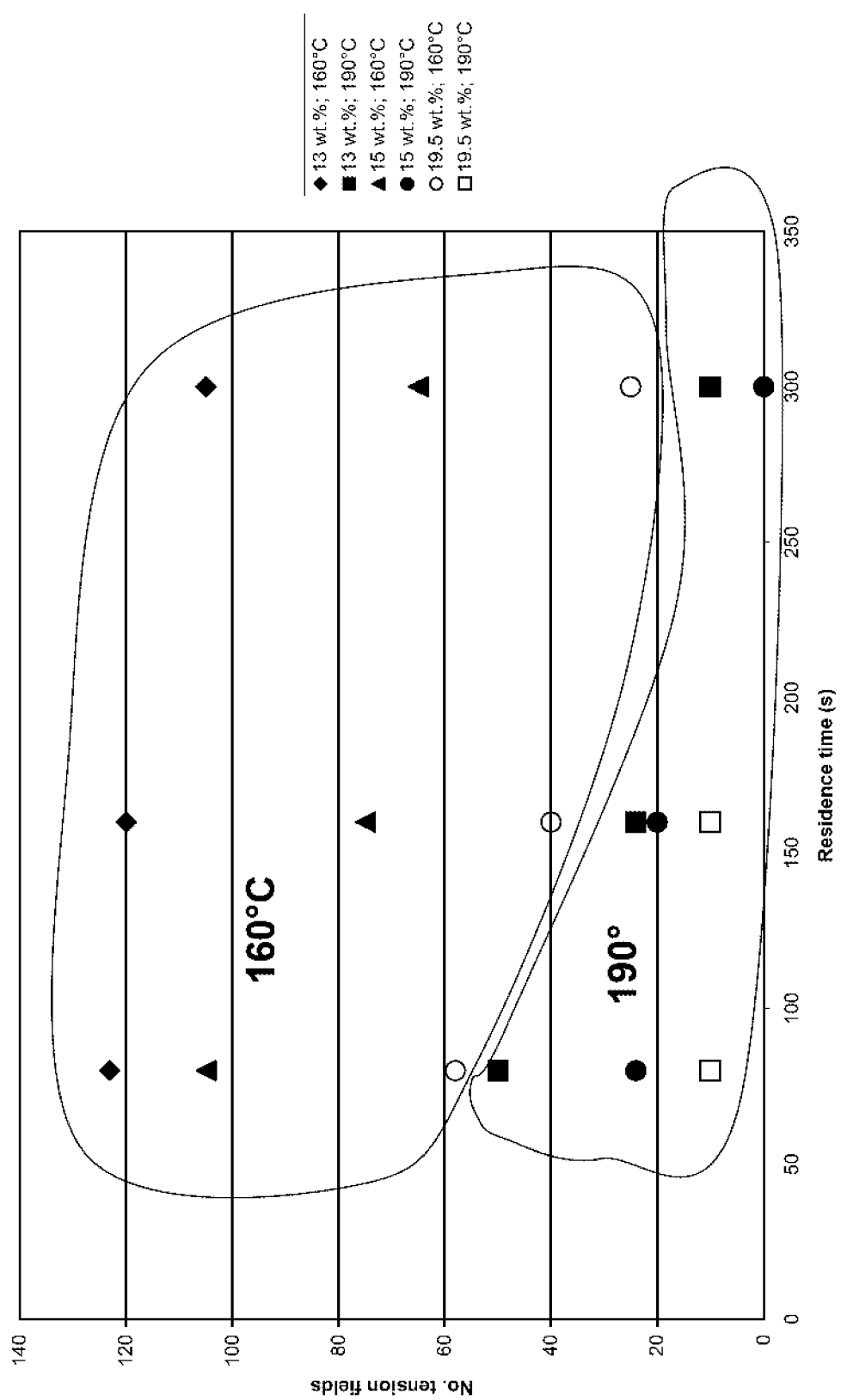

PARENTERAL FORMULATION

CROSS-REFERENCE TO RELATED APPLICATIONS

This application is a National Stage of PCT/NL2008/050121, filed Feb. 29, 2008, which claims the benefit and priority to U.S. Provisional Application No. 60/892,401, filed Mar. 1, 2007 and EPC 07103348.4, filed Mar. 1, 2007. The foregoing applications are incorporated by reference herein in their entirety.

FIELD OF THE INVENTION

The present invention relates to a kinetic implant comprising a biologically or pharmaceutically active substance for the delivery of said biologically or pharmaceutically active substance in or to a vertebrate, e.g. a mammal. The present invention further relates to a process for manufacturing the kinetic implant and to a process for loading the kinetic implant with a biologically or pharmaceutically active substance, wherein the biologically or pharmaceutically active substance is optionally stabilized by a stabilizing component.

BACKGROUND OF THE INVENTION

Injection is a common technique to deliver a biologically or pharmaceutically active substance, e.g. a vaccine or an antibiotic, to vertebrates such as mammals. However, the process of injection is cumbersome and causes many health problems around the world (cf. for example G.G.P. van de Wijdeven, "Development and assessment of mini-projectiles as drug kinetic implants", J. Controlled Release 85, 145-162, 2002). In the art, various systems have been developed which partially avoid such problems. In particular, such systems do often not require reconstitution of the biologically or pharmaceutically active material and do not involve any physical contact between the vertebrate and the delivery device. Examples of such techniques include ballistic delivery of, optionally biodegradable, bullets comprising the biologically or pharmaceutically active substance, or powders or microspheres comprising the biologically or pharmaceutically active substance. However, powders and microspheres have as a general disadvantage that they are less efficient than needles.

U.S. Pat. No. 3,948,263, incorporated by reference, discloses a veterinary ballistic implant comprising a biologically or pharmaceutically active substance, e.g. a vaccine. The implant may be made from non-biodegradable materials, e.g. polyolefins, or biodegradable materials, e.g. hydroxypropylcellulose. Similar implants are disclosed in for example U.S. Pat. No. 3,982,536 and U.S. Pat. No. 3,616,758, incorporated by reference herein.

U.S. Pat. No. 4,326,524, incorporated by reference, discloses a veterinary ballistic implant made of mixtures comprising solid, particulate, biologically or pharmaceutically active materials, preferably an antibiotic, and a binder, preferably a water soluble, thermoplastic, cohesive material such as hydroxypropyl cellulose, hydroxypropylmethyl cellulose, methyl cellulose, sodium carboxymethyl cellulose, polyvinyl alcohol, polyvinylpyrrolidone, gum arabic and the like. A preferred cellulose derivative is hydroxypropylcellulose due to its compatibility with biological systems, its cohesive characteristics and its thermoplasticity. The implant may be provided with a cavity for additional biologically or pharmaceutically active substances.

U.S. Pat. No. 4,449,982, incorporated by reference, discloses a veterinary ballistic implant having a cavity that is filled with a medicament. The medicament may for example be a vaccine, an antibiotic or a small electronic device. If the implant is used for delivering a medicament to an animal intended for human consumption, it is preferred that the implant is made from materials that can be assimilated by the animal body. An example of such a material is a blend of equal mixtures of calcium carbonate and hydroxypropyl cellulose.

WO 87/06129, incorporated by reference, discloses a veterinary ballistic implant comprising a plurality of biodegradable capsules, wherein the biodegradable capsules comprise an effective amount of a physiologically active ingredient, e.g. a vaccine. The implants may be made from materials having an adjuvant function, e.g. water soluble polymers such as polyvinyl pyrrolidone, said materials optionally comprising fillers and extenders. The capsules are preferably made from biologically or pharmaceutically degradable polymers comprising glycolic acid and/or lactic acid.

U.S. Pat. No. 4,664,664 and U.S. Pat. No. 6,375,971, incorporated by reference, disclose a ballistic implant for solid dose medicating of animals. The ballistic implant according to U.S. Pat. No. 6,375,971 comprises a biologically or pharmaceutically compatible bullet having a nose and a body, the latter defining an interior cavity having an interior wall. The surface of the interior wall is provided with means that provide enhanced friction. A cylindrical medicament payload having a size slightly greater than the diameter of the interior cavity is forced into the body of the biologically or pharmaceutically compatible bullet. The bullet is made of a biologically or pharmaceutically inert material that does not cause local tissue reactions and such materials include "GRAS" ("Generally Recognized As Safe"). Suitable GRAS materials are said to be cellulose derivatives, preferably those disclosed in U.S. Pat. No. 4,326,524, incorporated by reference herein. When inside animal's muscle tissue, the bullets are said to disintegrate within a few hours and almost always within 24 hours. The materials for manufacturing the bullet are preferably a polymer blend which may contain fillers, e.g. calcium carbonate, lubricants, e.g. stearic acid. The length of the bullet would not be critical, although longer bullets (i.e. longer than 0.825 inch≈2.096 cm) provide a better accuracy. However, the bullet disclosed in U.S. Pat. No. 6,375,971 has several disadvantages. First of all, the preferred materials for manufacturing the bullet, i.e. hydroxypropyl cellulose and similar materials, are known to have a poor biodegradability as is discussed in U.S. Pat. No. 6,001,385, incorporated by reference. In particular, such materials have undesired side-effects as they often cause inflammations and granulomas. Furthermore, materials like calcium carbonate and stearic acid are known to have an adjuvating effect which is undesired when the implant is intended for human application. Another important disadvantage of the bullet is that the interior surface thereof must be provided with means that provide enhanced friction which requires complicated production steps. Additionally, the size and weight of the bullets according to U.S. Pat. No. 6,375,971 are such that they have too much kinetic energy when fired and are therefore too awkward to be used for human purposes as will be explained in more detail below. Consequently, the bullets disclosed in U.S. Pat. No. 6,375, 971 are not very useful and in particular not in human applications.

U.S. Pat. No. 6,001,385, incorporated by reference, and G.G.P. van de Wijdeven, "Development and assessment of mini-projectiles as drug kinetic implants", J. Controlled Release 85, 145-162, 2002, disclose ballistic implants made of fully destructurised starch, said ballistic implants comprising a biologically or pharmaceutically active material. However, fully destructurised starch (which is the same material as the thermoplastic starch disclosed in G. G. P. van de Wijdeven, "Development and assessment of mini-projectiles as drug kinetic implants", J. Controlled Release 85, 145-162, 2002) is produced from starch that is subjected to a heat treatment that heats the starch to a temperature above its glass transition and melting temperatures. It has therefore a poor cytotoxicity and poor in vivo degradability properties, presumably due to recrystallisation of the macromolecules formed during the destructurising process thereby making these macromolecules insusceptible or unreachable for hydrolysing enzymes. Additionally, the ballistic implants according to U.S. Pat. No. 6,001,385 do not show tension fields under a polarised light microscope. The relevance of tension fields with respect to biodegradability is discussed in more detail below.

U.S. Pat. No. 6,811,792, incorporated by reference, discloses a solid dosage delivery vehicle suitable for ballistic delivery comprising an outer portion, said outer portion comprising a water soluble, glassy and/or polymeric material, and an hollow compartment comprising a stabilising polyol, most preferably trehalose, and a biologically or pharmaceutically active substance, e.g. a vaccine. Suitable water soluble glasses are said to be those disclosed in WO 90/11756. Preferably, the water soluble glass is a carboxylate derivative of a polyol or a carbohydrate derivative, e.g. trehalose and trehalose octaacetate. The polymeric material may be a polymer or copolymer comprising lactide, glycolide or glucuronide or another polyester, a polyorthoester or a polyanhydride. The compositions used for making the outer portion of the solid dosage delivery vehicle have typically a slow degradation rate which implies that the biologically or pharmaceutically active substance is released in a sustained manner during a period in the order of at least days. The solid dosage delivery vehicle may be in the form of a needle having a diameter in the range of 1-5 µm and a length in the range of 5-150 µm. However, such needles are impractical due to their small size, low weight and low strength.

EP 326.517 A1, incorporated by reference, discloses a process for forming starch into a melt wherein a composition comprising starch and water and having a water content of 5 to 40 wt. %, calculated on the weight of the composition, is extruded at a temperature of 80° to 200,preferably 120° to 190°, more preferably 130° to 190° C., and a pressure of 0 to 15 MPa, preferably 0 to 7.5 MPa and in particular 0 to 5 MPa. The obtained essentially destructurised starch has a water content of 10 to 20 wt. %, more preferably 12 to 19 wt. % and in particular 14 to 18 wt. %. Residence times of the composition within the extruder and mechanical properties of the essentially destructurised starch are not disclosed.

WO 92/15285 discloses that starch melts can be processed to various levels of destructurisation ranging from destructurised starch, molecularly dispersed starch (i.e. a higher level of destructurisation) and thermoplastic starch. It further discloses that the method disclosed in U.S. Pat. No. 4,673,438 (equivalent to EP 118.240 A1) provides substantial destructurisation. The process according to WO 92/15285 involves a temperature of 80° to 240° C., preferably 130° to 160° C., wherein a water content is maintained in the range of 5 to 45 wt. %, preferably 10 to 25 wt. %. Example 1 discloses the extrusion of a mixture comprising potato starch (81% w/w), hydrogenated triglyceride (1% w/w), soya lecithine (0.5% w/w), titanium dioxide (0.5% w/w) and water (17% w/w) following the procedure of U.S. Pat. No. 4,673,438.Example 2 and FIG. 6 disclose that compositions comprising the starch product and a pharmaceutically active substance released the latter more rapidly at higher water contents (ranging from 5% to 17.7%). Example 11 discloses that the degree of destructurisation can be controlled by process parameters (temperature, water content of the starch, amount of shear and processing time) without specifying the effect of these process parameters. FIG. 10 discloses that within a process temperature range of 100° to 160° C. no differences within release rates was observed when compositions comprising the starch product and a pharmaceutically active substance were subjected to a dissolution test. Only when the process temperature employed was 70° C., a more rapid release was observed. Furthermore, mechanical properties of the destructurised starch are not disclosed.

The present invention therefore provides a ballistic or kinetic implant having excellent mechanical properties which rapidly degrades under physiological conditions and which has a very low cytotoxicity.

SUMMARY OF THE INVENTION

The present invention relates to a kinetic implant comprising:
(a) a biodegradable material comprising opened starch, destructurised starch or a mixture of opened starch and destructurised starch;
(b) a biologically or pharmaceutically active substance; and
(c) a stabilising component stabilising the biologically or pharmaceutically active substance.

BRIEF DESCRIPTION OF FIGURE 1

FIG. 1 shows the number of tension fields per 3.2 $cm^2$ observed in tensile bars made of opened starch as function of the residence time in the extrusion process (at constant water content of the starch and at constant extrusion temperature). The extrusion pressure was fixed at 14 MPa. Data are taken from Tables 6 and 7.

DETAILED DESCRIPTION OF THE INVENTION

Definitions and Expressions

The term "chemically non-modified starch" is to be understood as a native starch material that is obtained from seeds and cereals, e.g. corn, waxy corn, high amylose corn, oats, rye, maize, wheat and rice, or roots, e.g. potato, sweet potato and tapioca. Preferably, the starch material is potato starch, maize starch or corn starch, most preferably potato starch. The term "chemically non-modified starch" also includes physically modified starch materials or mechanically modified starch materials. Physical modification can be achieved by e.g. cooking or gelatinisation whereas mechanical modification can be achieved by dry grinding. However, according to the invention, it is preferred that the starch material is not physically modified. It is further well known that the main components of native starch material are amylose and amylopectine, the molecular weights thereof being dependent from the origin of the starch (cf. for example Kirk-Othmer, Encyclopedia of Chemical Technology, Vol. 22, 699-719, 1997).

The prior art, in particular in EP A 774.975, incorporated by reference herein, discloses "destructurised starch" and "substantially destructurised starch" which implies that essentially all starch particles are destructurised, i.e. all starch granules are disrupted and within the disrupted starch granules, the starch molecules are dispersed. In this document, the materials "destructurised starch" and "substantially destructurised starch" are indicated by the generic term "destructurised starch" for convenience.

The present invention, however, relates inter alia to "opened" starch which is a materially different product. "Opened" starch is characterised by partly disruption of the starch granules, whereby at least a small part of packages of the molecules within the granules retain their original radiary structure, i.e. that starch granules swell, get opened, may leak amylose but not amylopectin. In opened starch, the amylopectin layers stay at least partly intact, although the hydrogen bonds that were originally present in between the amylopectine layers are broken. Whereas destructurised starch is obtained at relatively high temperatures and/or relatively long residence times and/or high shear and/or low water contents during processing within the extruder and/or an injection moulding machine, opened starch is obtained at less harsh, more subtle processing conditions: in general higher water contents, less shear, shorter residence time during processing, lower temperatures, higher pressures, followed by "ripening" of the extrudate.

Opened starch has an increased susceptibility for enzymes which is due to the fact that in opened starch granules the macromolecules can be reached by the proteineous enzymes, whereas in destructurised starch granules enzymes can only reach the macromolecules with great difficulty. This is caused by the fact that opened starch is capable of absorbing aqueous fluids, e.g. water, very rapidly and in high quantities (until fifty times its own weight) whereas substantially destructurised starch hardly absorbs aqueous fluids.

The difference between these materials can for example first be demonstrated by the number of tension fields in shaped articles and test specimen made of destructurised starch and shaped articles and test specimen made from opened starch as will be explained in more detail below. In principle, shaped articles and test specimen made of completely destructurised starch do hardly show tension fields and these products appear to be less susceptible to enzymatic degradation. In contrast, shaped articles and test specimen made of opened starch show a relatively high number of tension fields and are far more easily degraded by enzymatic action which is advantageous in certain applications, in particular in pharmaceutical, neutraceutical and implantation applications. Secondly, the increased susceptibility for enzymes is due to the fact that in opened starch granules the macromolecules (such as the amylopectin layers that are no longer interconnected by broken hydrogen bonds) can be reached by the proteineous enzymes, whereas in native starch granules enzymes cannot reach the macromolecules, and whereas in substantially (on molecular level) destructurised starch these molecules recrystallise thereby making the macromolecules unreachable for enzymes. According to the present invention, opened starch is characterized by at least 2, preferably at least 5, more preferably at least 10, even more preferably at least 25 and most preferably at least 50 tension fields/3.2 $cm^2$ as determined by visual inspection of tensile bars 5 mm wide and 2 mm thick which are made of opened starch using a standard polarised light stereomicroscope. Destructurised starch is therefore characterized by less than 2 tension fields/3.2 $cm^2$, in particular less than 1 tension field/ 3.2 $cm^2$.

The term "biologically or pharmaceutically active substance" includes any substance that has a biological effect or response when it is administered to a living organism (in particular a vertebrate) or when a living organism is exposed in some way to the biologically or pharmaceutically active substance. Consequently, the term "biologically or pharmaceutically active substance" includes pharmaceutical agents, therapeutic agents and prophylactic agents. Suitable examples of pharmaceutical agents are antiinflammatory drugs, analgesics, antiarthritic drugs, antispasmodics, antidepressants, antipsychotics, tranquilizers, antianxiety drugs, narcotic antagonists, antiparkinsonism agents, cholinergic agonists, chemotherapeutic drugs, immunosuppressive agents, antiviral agents, antibiotic agents, appetite suppressants, antiemetics, anticholinergics, antihistaminics, antimigraine agents, coronary, cerebral or peripheral vasodilators, hormonal agents, contraceptives, antithrombotic agents, diuretics, antihypertensive agents, cardiovascular drugs and opioids. Suitable examples of therapeutic and prophylactic agents are subcellular compositions, cells, bacteria, viruses, molecules including lipids, organic compounds, proteins and (poly)peptides (synthetic and natural), peptide mimetics, hormones (peptide, steroid and corticosteroid), D and L amino acid polymers, oligosaccharides, polysaccharides, nucleotides, oligonucleotides and nucleic acids, including DNA and RNA, protein nucleic acid hybrids. Suitable examples of proteins and (poly) peptides are enzymes, biopharmaceuticals, growth hormones, growth factors, insulin, monoclonal antibodies, interferons, interleukins and cytokines Suitable examples of prophylactic agents are immunogens such as vaccines, e.g. live and attenuated viruses, nucleotide vectors encoding antigens, bacteria, antigens. Vaccines may be produced by molecular biology techniques to produce recombinant peptides or fusion proteins containing one or more portions of a protein derived from a pathogen. The biologically or pharmaceutically active substance may be derived from natural sources or may be made by recombinant or synthetic techniques.

The term "stabilising component stabilising the biologically or pharmaceutically active substance" includes components that are capable to prevent or inhibit deactivating processes, e.g. denaturation or decomposition, of the biologically or pharmaceutically active substance. Deactivating processes result into a reduced biological effect or response which is obviously undesired. Such processes may occur during the manufacture of a kinetic implant comprising a biologically or pharmaceutically active substance, during loading of a kinetic implant with a biologically or pharmaceutically active substance or upon storage or during use of a (loaded) kinetic implant.

The verb "to comprise" as is used in this description and in the claims and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there is one and only one of the elements. The indefinite article "a" or "an" thus usually means "at least one".

Destructurised Starch

Destructurised starch and processes for making destructurised starch are well known in the art and are for example disclosed in EP A 118.240, EP A 282.451, EP A 298.920, GB A 2.190.093, EP A 304.401, EP A 474.705, EP 495.056, EP A 774.975 and EP A 994.564, all incorporated by reference herein. In these processes, starch, a plasticizer, e.g. water, and optionally other components are extruded under relatively severe conditions, e.g. high pressures and temperatures and long residence times. However, according to the present invention, it is preferred that the destructurised starch is made from starch and a plasticizer, wherein it is preferred that the plasticizer is water. Preferably, the starch is a chemically non-modified starch.

The destructurised starch comprises preferably about 10 to about 25 wt. % of water, preferably about 11 wt. % to about 22 wt. %, more preferably about 12 wt. % to about 20 wt. %, based on the total weight of the destructurised starch.

The degree of destructurisation is dependent from the process conditions and may vary between "slightly destructurised starch" to "substantially fully destructurised starch". Most preferably, the destructurised starch is manufactured by the method disclosed in Example 1 of EP A 774.975.

Opened Starch

Opened starch and processes for making opened starch are, however, unknown in the art. As disclosed above, a very typical and important feature of the material designated opened starch, is that shaped articles, e.g. kinetic implants, made thereof have tension fields. It was surprisingly found that the presence of tension fields is correlated to the in vivo degradation rate of shaped articles made from opened starch according to the invention, the destructurised starch known from the prior art, and from mixtures of opened starch and destructurised starch. Furthermore, the number of tension fields was found to decrease to a negligible number, i.e. almost zero, when only destructurised starch was used. As a consequence, process conditions have been designed that provide a biodegradable material and kinetic implants made thereof having excellent properties, in particular with respect of mechanical properties, (cyto)toxicity properties and in vivo degradability. In addition, biodegradability of kinetic implants could be tuned by using mixtures of opened starch and destructurised starch.

Tension fields could be made visible in shaped articles such as kinetic implants and test specimen formed from the opened starch according to the present invention by visual inspection of the shaped articles and the test specimen with the aid of polarised light. The number of tension fields in the shaped articles and test specimen was determined by counting and the counted number correlated well to the biodegradability (in vivo and in vitro) of the shaped article or test specimen. For example, it appeared that if the shaped article is a solid bullet-like article as for example disclosed in EP A 774.975, but made from opened starch according to the present invention, the number of tension fields is far higher than when made from the destructurised starch known from the prior art.

The opened starch according to the present invention comprises preferably about 10 to about 25 wt. % of water, preferably about 11 wt. % to about 22 wt. %, more preferably about 12 wt. % to about 20 wt. %, based on the total weight of the opened starch.

The opened starch according to the present invention is preferably manufactured by a process wherein in a first step a chemically non-modified starch comprising about 15 wt. % to about 50 wt. % water, preferably about 25 wt. % to about 45 wt. % based on the total weight of the chemically non-modified starch, is extruded in the presence of a plasticizer, the plasticizer being water, at a temperature of about 30° to about 150° C., preferably about 50° to about 130° C., more preferably about 60° to about 110° C., and a pressure of about 45 to about 250 bar (about 4,5 to about 25 MPa), preferably about 70 to 200 bar (about 7 to about 20 MPa), to form a granulate. The amount of plasticizer added is preferably about 20 wt. % to about 50 wt. %, more preferably about 25 wt. % to about 45 wt. %, based on the total weight of chemically non-modified starch and the plasticizer. The residence time of the chemically non-modified starch and the plasticizer in the heating zones of the extruder is preferably about 0.1 to about 7 minutes, more preferably about 0.2 minute to about 5 minutes and most preferably about 0.2 minute to less than about 5 minutes. The relative high water content is advantageous since lower pressures (because in excess of water, the hydrogen bonds between the layers of starch molecules can more easily be loosened without loosing the molecular arrangement within the opened starch granule) and lower shear than normally applied in the manufacturing process of the biodegradable material can be employed.

It is preferred that the weight average molecular weight of the chemically non-modified starch is greater than 20.000.000. More preferably, the weight average molecular weight of the chemically non-modified starch is greater than 20.000.000 up to 200.000.000.

The water content of the opened starch according to the present invention at this stage of the manufacturing process, i.e. the granulate, is preferably about 20 wt. % to about 50 wt. %, more preferably about 25 wt. % to about 45 wt. %, based on the total weight of the opened starch. At this stage of the process, the water content of the opened starch (granulate) is higher when compared with the water content of the chemically non-modified starch used as starting material.

According to the present invention, it is preferred to further subject the first granulate to an annealing step or a conditioning step, wherein the water content of the opened starch is reduced to about 10 to about 25 wt. %, preferably about 13 wt. % to about 19.5 wt. %, more preferably about 15.5 wt. % to about 17.5 wt. %, based on the total weight of the opened starch. This annealing step or conditioning step can be performed at a temperature of about 10° to about 80° C. This annealing step or conditioning step is further preferably performed for a period of about 0.2 to about 48 h, more preferably about 1 to about 3 h, followed by a ripening process of about at least 24 hours at room temperature. This annealing step is beneficial for an evenly distribution of the plasticizer through the opened starch.

The opened starch is rapidly degraded by enzymatic action. Kinetic implants solely made of opened starch disintegrate within minutes in vitro. Almost complete degradation occurs within two hours after application which is very advantageous since any material that is present subcutaneously or intramuscularly is likely to act as a locus resistentiae minoris which may result in local growth of bacteria and subsequent local inflammation of tissue. These local inflammations may result in systemic inflammations (metastasis to cause arthritis, endocarditis and meningitis). Such problems are for example disclosed in US 2006/121083, incorporated by reference herein.

Consequently, according to a preferred embodiment of the present invention, the opened starch is prepared according to a process wherein:

(a) in a first step a chemically non-modified starch comprising about 15 wt. % to about 50 wt. % water, based on the total weight of the chemically non-modified starch, is extruded in the presence of a plasticizer, the plasticizer being water, at a temperature of about 30° to about 150° C. and a pressure of about 45 to about 250 bar (about 4.5 to about 25 MPa) to form a granulate; and (b) optionally, but preferably in a second step the granulate is annealed or conditioned, preferably for a period of about 0.2 to about 48 h, to form the opened starch, wherein the water content of the opened starch is about 10 to about 25 wt. % of water, based on the total weight of the opened starch.

Hence, the present invention also relates to an opened starch obtainable by this process.

Like in the process for the preparation of destructurised starch, common additives which are well known in the art may be used in the process for the preparation of opened starch, provided that these additives do not have an adverse effect on mechanical properties, (cyto)toxicity properties and in vivo degradability properties and do not induce undesired adverse side effects such as e.g. inflammations and formation of granulomas. Such common additives include texturising agents, lubricants/release agents, melt flow accelerators and mixtures thereof. An example of a suitable texturising agent is titanium dioxide. Suitable examples of lubricants/release agents are animal fats, vegetable fats or mixtures thereof, Suitable melt flow accelerators are monoglycerides, diglycerides and mixtures thereof, and phosphatides, wherein it is preferred that the monoglycerides and diglycerides are derived from long-chained fatty acids, preferably $C_{14}$, $C_{16}$, $C_{18}$ fatty acids and wherein it is preferred that the phosphatide is a lecithin. When used, it is preferred that the amount of texturising agent is about 0.01% to about 1.0% by weight, preferably 0.02% to about 1.0% by weight, based on the total weight of the chemically non-modified starch and plasticizer. The preferred amount of the lubricant/release agent is about 0.4% to about 5.0% by weight, preferably about 0.8 to about 2.0% by weight, based on the total weight of the chemically non-modified starch and plasticizer. The preferred amount of the melt flow accelerator is about 0.01% to about 5.0% by weight, preferably about 0.05 to about 2.0 by weight, based on the total weight of the chemically non-modified starch and plasticizer.

The opened starch according to the present invention comprises processed amylose and processed amylopectine. The processed amylose and processed amylopectine in the opened starch each can be individually analysed. Compared to amylose and amylopectine of the chemically non-modified starch, the processed amylose and processed amylopectine in the opened starch may have undergone alterations and are therefore indicated by the adjective 'processed'.

The processed amylopectine of the opened starch according to the present invention has preferably a weight average molecular weight of about 20.000.000 to about 100.000.000 as determined by MALLS (Multi Angle Laser Light Scattering) on samples that were obtained after DMSO solubilisation and precipitation in alcohol. By the term "processed" in this document regarding the amylose and amylopectine components, it is intended to indicate that these components may be different from the amylose and amylopectine as they occur in the chemically non-modified starch, i.e. that during processing some degradation or modification may have occurred. The molecular weight distribution $M_w/M_n$ of the processed amylose is preferably in the range of about 2 to about 3. The weight average molecular weight of the processed amylose is preferably in the range of about 500.000 to about 2.000.000.

The Biodegradable Material

The biodegradable material according to the present invention comprises opened starch, destructurised starch or a mixture thereof. Preferably, the biodegradable material according to the invention comprises 50-100 wt. % of opened starch, destructurised starch or a mixture of opened starch and destructurised starch, more preferably 70-100 wt. %, even more preferably 80-100 wt. %, yet even more preferably 90-100 wt. %, based on the total weight of the biodegradable material. These weight percentages of opened starch and destructurised starch include the water contents mentioned above for opened starch and destructurised starch. The remainder of the biodegradable material, i.e. 0-50 wt. %, preferably 0-30 wt. %, even more preferably 0-20 wt. %, yet even more preferably 0-10 wt. %, based on the total weight of the biodegradable material, comprises other components selected from the group of cellulose, cellulose derivatives and analogues and biodegradable synthetic polymers and copolymers. According to a particularly preferred embodiment of the invention, the biodegradable material consists only of opened starch or a mixture of opened starch and destructurised starch. According to a particularly preferred embodiment of the present invention, the biodegradable material consists only of opened starch, destructurised starch or a mixture of opened starch and destructurised starch.

According to a preferred embodiment of the present invention, the biodegradable material comprises a mixture of opened starch and destructurised starch, wherein the weight ratio of opened starch to destructurised starch is preferably between 100:0 and 1:99, more preferably between 100:0 and 50:50, even more preferably between 100:0 and 75:25 and most preferably between 100:0 and 80:20,based on the total weight of the biodegradable material. Higher amounts of opened starch are generally preferred when a rapid biodegradability of the biodegradable material is desired and a reduction of risks of side-effects, e.g. inflammations and formation of granulomas, is necessary.

The biodegradable material according to the present invention has further a bulk density of about 1.0 to about 1.5 kg/dm$^3$, preferably about 1.2 to about 1.5 kg/dm$^3$.

The biodegradable material according to the present invention is preferably a granulate which enables easy further processing. Additionally, the biodegradable material according to the present invention has a tensile strength of at least about 20 N/mm$^2$ as determined with test specimen made from the biodegradable material by injection moulding, wherein the tensile strength was determined on a Zwick testing machine of the type Z 2.5. Obviously, the tensile strength is dependent from the storage conditions, e.g. relative humidity and storage time, of the biodegradable material and of the test specimen. However, evaluation of test specimen of the biodegradable material has shown that tensile strengths up to about 70 N/mm$^2$ can be attained. Consequently, the biodegradable material according to the present invention has a tensile strength of at least about 20 N/mm$^2$ up to about 70 N/mm$^2$.

In certain applications, for example if a relatively slow degradation of the kinetic implant is necessary as in sustained release and side-effects are considered acceptable, it may be desired that the biodegradable material comprises other components which have been used in the prior art. Such components include materials such as hydroxypropyl cellulose and "biodegradable" synthetic polymers or copolymers comprising one or more monomers selected from the group consisting of hydroxyl alkanoates wherein the alkyl group comprises 1 to 12 carbon atoms, lactide, glycolide, ε-caprolactone, 1,4-dioxane-2-one, 1,5-dioxepan-2-one, trimethylene carbonate (1,3-dioxane-2-one) and mixtures thereof, wherein it is generally preferred that the copolymer is a random copolymer or a block copolymer and wherein the block copolymer is preferably a diblock copolymer or a triblock copolymer. Such polymers and copolymers are well known in the art and are for example disclosed in U.S. Pat. Nos. 2,668,162, 2,703,316, 3,636,956, 3,839,297, 4,137,921, 4,157,437, 4,243,775, 4,443,430, 5,076,983, 5,310,865 and 6,025,458, all incorporated by reference herein. As will be apparent to those skilled in the art, the degradation can also be controlled by varying the weight ratio of opened starch and destructurised starch.

The present invention also relates to a process for preparing a biodegradable material, said biodegradable material comprising about 50 to about 100 wt. % of opened starch, destructurised starch or of a mixture of opened starch and destructurised starch, based on the total weight of the biodegradable material, said biodegradable material having a bulk density of 1.0 to 1.5 kg/dm$^3$, wherein:

(a) an opened starch is made by extruding a chemically non-modified starch comprising about 15 wt. % to about 50 wt. % water, based on the total weight of the chemically non-modified starch, in the presence of a plasticizer, the plasticizer being water, at a temperature of about 30° to about 150° C. and a pressure of about 4.5 to about 25 MPa to form a granulate, the amount of plasticizer added being about 20 wt. % to about 50 wt. %, based on the total weight of chemically non-modified starch and the plasticizer, and (b) optionally mixing the opened starch with a destructurised starch.

It is preferred that the opened starch and the destructurised starch are mixed with a weight ratio of opened starch to destructurised starch of between 100:0 and 1:99, more preferably between 100:0 and 50:50, even more preferably between 100:0 and 75:25 and most preferably between 100:0 and 80:20, based on the total weight of the biodegradable material. However, as is disclosed above, the biodegradable material may also comprise only opened starch or only destructurised starch, wherein the opened starch is prepared according to step (a) shown above and wherein the destructurised starch is prepared according to the method disclosed in Example 1 of EP A 774.975.

The Stabilising Component

The stabilising component according to the present invention provides long term storage stability as well as thermostability to the biologically or pharmaceutically active substance. The stabilising component according to the present invention is preferably a polyol, more preferably a carbohydrate, e.g. a monosaccharide, a disaccharide, a trisaccharide, an oligosaccharide or a polysaccharide. The polysaccharide may be a heteropolysaccharide or a homopolysaccharide. The carbohydrates may occur in an optical pure state or may be mixtures of different enantiomers, e.g. a racemic mixture, or of enantiomeric different substructures, i.e. that e.g. polysaccharides comprise various monomers that occur in an enantiomeric different form or forms. The carbohydrate may occur in an acyclic form or a cyclic form, e.g. aldose, ketose, furanose, pyranose forms, or a mixture thereof. Oligo- and polysaccharides may be linear or branched. The carbohydrate may also occur in the form of a conjugate, e.g. glycoproteins, proteoglycans, peptidoglycans, glycolipids, lipopolysaccharides and phosphonomannans. The carbohydrate may also be a derivative, e.g. a sugar alcohol or a hydrate, of the carbohydrate. Suitable examples of stabilising carbohydrates are ribose, glucose, fructose, mannose, galactose, maltose, lactose, sucrose, inulin and the like. The carbohydrate is preferably a disaccharide, more preferably a non-reducing disaccharide and most preferably a trehalose ($\alpha$-D-glucopyranosyl-$\alpha$-D-glucopyranoside). Trehalose is known to stabilise biologically or pharmaceutically active substances such as proteins and viruses as is in detail disclosed in e.g. U.S. Pat. No. 6,811,792, incorporated by reference herein.

The Kinetic Implant

According to the present invention, there are various embodiments of the kinetic implant. According to a first preferred embodiment, the kinetic implant is made from a biodegradable material, a biologically or pharmaceutically active substance and a stabilising component, wherein the biodegradable material comprises opened starch, destructurised starch or a mixture thereof.

According to a second preferred embodiment, the kinetic implant is made from a biodegradable material, a biologically or pharmaceutically active substance and optionally a stabilising component, wherein the biodegradable material comprises a mixture of opened starch and destructurised starch. However, it is preferred that in this second preferred embodiment the stabilising component is also present.

According to a third preferred embodiment, the kinetic implant is made from a biodegradable material, a biologically or pharmaceutically active substance and optionally a stabilising component, wherein the biodegradable material consists of opened starch. However, it is preferred that also in this third preferred embodiment the stabilising component is present.

The biodegradable material used for making the kinetic implant according to these embodiments may therefore be constituted as is disclosed above.

In these first, second and third preferred embodiments, the biologically or pharmaceutically active substance and the stabilising component may be homogeneously dispersed within the biodegradable material. Alternatively, the kinetic implant may comprise an inner, hollow portion, said inner, hollow portion comprising the biologically or pharmaceutically active substance and the optional stabilising component. More preferably, the kinetic implant comprises an inner, hollow portion as such an embodiment allows for a better stabilisation of the biologically or pharmaceutically active substance as will be elucidated below. Kinetic implants having an inner, hollow portion are for example disclosed in EP A 774.975, incorporated by reference.

According to the present invention, it is further preferred that the kinetic implant having an inner, hollow portion has an average wall thickness of about 10 μm to about 2500 μm, preferably about 30 μm to about 1500 μm, more preferably about 50 μm to about 500 μm. Preferably, the kinetic implant is provided with a conical tip and a hollow bottom end, although it is obviously possible to provide the hollow kinetic implant with a closing means after it is loaded with the biologically or pharmaceutically active substance and the optional stabilising agent as is disclosed in EP A 774.975.

Most preferably, the wall region of the inner, hollow portion is provided with a coating or layer comprising the biologically or pharmaceutically active substance and the optional stabilising component, wherein a part of said wall region is coated or impregnated by a coating formulation comprising the biologically or pharmaceutically active substance and the optional stabilising component upon application of the coating formulation on the wall region of the inner, hollow portion of the kinetic implant according to the present invention. This latter embodiment permits the use of lower amounts or even the absence of the stabilising component. Optionally, the inner, hollow portion of this second embodiment may comprise one or more compartments.

Preferably, a major part of the wall region is coated or impregnated by the coating formulation. As will be understood by the person skilled in the art, the wall region of the inner, hollow portion of the kinetic implant has a relatively great surface area: if the inner, hollow portion of the kinetic implant is considered as a hollow cylinder with open ends, the surface area is $2\pi r h$ which implies that the inner wall of a hollow kinetic implant having a diameter of about 3 mm, a length of about 17 mm and a wall thickness of about 350 μm, has a surface area of about 1.4 $cm^2$. Consequently, coating or impregnating a major part of the wall region of the inner, hollow portion of the kinetic implant allows for applying a thin coating or layer comprising the biologically or pharmaceutically active substance and the stabilising component wherein the biologically or pharmaceutically active substance and the stabilising component are in intimate contact thereby allowing for an efficient stabilisation of the biologically or pharmaceutically active substance.

In general, a kinetic implant having an inner, hollow portion is preferred over a solid kinetic implant in which the biologically or pharmaceutically active substance and the optional stabilising component are homogeneously dispersed within the biodegradable material, in particular when the biologically or pharmaceutically active substance is less stable under the conditions of the manufacturing process of the kinetic implant.

According to the present invention, the kinetic implant has a length:diameter ratio of more than 4, provided that the length of the kinetic implant is between 1 mm to 50 mm. More preferably, the length:diameter ratio is 5 or more. However, the upper limit of the length:diameter ratio is about 500 and is preferably less than about 100, more preferably less than about 75 and most preferably less than about 50. The length of the kinetic implant is preferably 2 mm to 25 mm, more preferably 6 mm to 25 mm.

According to a particular preferred embodiment, the kinetic implant is made from the biodegradable material according to the present invention, wherein the biodegradable material comprises opened starch, destructurised starch or a mixture of opened starch and destructurised starch. In this particular preferred embodiment, the weight ratio of opened starch and destructurised starch in the mixture is preferably between 100:0 and 1:99, more preferably between 100:0 and 50:50, even more preferably between 100:0 and 75:25 and most preferably between 100:0 and 80:20, based on the total weight of the biodegradable material.

Preferably, the biodegradable material comprises 50-100 wt. % of opened starch, destructurised starch or of a mixture of opened starch and destructurised starch, based on the total weight of the biodegradable material. More preferably, the biodegradable material comprises 50-100 wt. % of opened starch, destructurised starch or of a mixture of opened starch and destructurised starch, more preferably 70-100 wt. %, even more preferably 80-100 wt. %, yet even more preferably 90-100 wt. %, based on the total weight of the biodegradable material. Most preferably, the biodegradable material consists only of opened starch, in particular when a rapid biodegradation is desired.

The kinetic implant is suitable for the parenteral delivery of biologically or pharmaceutically active substances. Parenteral delivery includes delivery by injection or infusion which may be intravenous, intraarterial, intramuscular, intracardiac, subcutaneous, intradermal, intrathecal, transdermal, and transmucosal. Preferably, the kinetic implant is used for intramuscular, subcutaneous and transdermal delivery.

The weight of the kinetic implant is preferably such that the kinetic implant can be provided with an amount of kinetic energy in the range of about 0.1 to about 10 J, preferably about 0.2 to about 5 J. This implies that, if the kinetic implant is accelerated to a velocity comparable to the sound velocity (in dry air at about 20° C., the sound velocity is about 340 m/s), the minimum weight is about 1 mg whereas the maximum weight is about 180 mg. However, for human applications, it is in particular preferred that the kinetic energy ((based on a velocity of about 340 m/s) of the kinetic implant is in the range of 0.1 to 5 J, preferably 0.1 to 3 J. If higher kinetic energies (based on a velocity of about 340 m/s) are employed, the kinetic implant becomes too awkward for human application. In contrast, kinetic implants as disclosed in U.S. Pat. No. 3,982,536 and U.S. Pat. No. 3,616,758 which are commercialized by Solid Tech Animal Health, Inc., under the trade name Biobullet® have a kinetic energy (based on a velocity of about 340 m/s) of about 10 to about 50 J (corresponding weight of about 500 to about 2000 milligrams) and are therefore unsuitable for at least human applications.

When unloaded with a biologically or pharmaceutically active substance, the kinetic implant according to the present invention is preferably manufactured by injection moulding, wherein the biodegradable material according to the present invention is subjected to injection moulding at a pressure of about 500 to about 3000 bar (about 50 to about 300 MPa), preferably about 600 to about 2500 bar (about 60 to about 250 MPa), and a temperature of about 100° to about 200° C., preferably about 150° to about 190° C., with residence times of about 5 seconds to about 300 seconds.

Shaped articles made of opened starch, when solubilised at ambient temperature (i.e. about 15° to about 25° C.) in about 50% in DMSO/water, wherein the ratio DMSO:water is 9:1, preferably have a weight average molecular weight of processed amylopectine of about 5.000.000 to about 25.000.000 as determined by MALLS and a weight average molecular weight of processed amylose of about 200.000 to about 1.000.000 as determined by GPC-MALLS-RI. In contrast, the weight average molecular weight of amylose in shaped articles made of destructurised starch is much lower than 200.000, e.g. about 120.000, and the weight average molecular weight of amylopectine in shaped articles made of destructurised starch is much lower than 5.000.000, e.g. about 1.000.000. Consequently, although the injection moulding step reduces the weight average molecular weight of amylose and amylopectine in both opened starch and destructurised starch, the lower values observed in destructurised starch are due to the harsh conditions employed in the preparation of destructurised starch.

According to the present invention, kinetic implants loaded with a biologically or pharmaceutically active substance can be manufactured as follows. According to a first method, the kinetic implant is manufactured by subjecting a composition of the biodegradable material, the biologically or pharmaceutically active substance and the optional stabilising component to injection moulding, preferably at a pressure of about 500 to about 3000 bar and a temperature of about 100° to about 200° C., provided that the biologically or pharmaceutically active substance does not substantially degrade under the processing conditions. According to a second, more preferred method, a kinetic implant having a hollow portion is formed. In an optional subsequent step, the kinetic implant is sterilised. Suitable sterilisation techniques are well known in the art and include gamma irradiation, beta irradiation, ultraviolet irradiation, treatment with ethylene oxide gas, hydrogen peroxide plasma sterilisation and the like. Next, the kinetic implant is loaded with a composition comprising the biologically or pharmaceutically active substance and the optional stabilising component.

According to a preferred embodiment, the composition comprising the biologically or pharmaceutically active substance and the optional stabilising component is a liquid composition and therefore comprises one or more solvents, preferably water. In a final step, the solvent is then removed which in the case of water can conveniently be accomplished by techniques well known in the art, e.g. freeze drying or vacuum drying. After drying, the water content of the kinetic implant is in the range of about 0.1 wt. % to about 8 wt. %, based on the total weight of the kinetic implant.

Accordingly, the present invention also provides a method for loading a kinetic implant having an inner, hollow portion, said inner, hollow portion having a wall region, with a biologically or pharmaceutically active substance, wherein:

(a) said kinetic implant is optionally subjected to a sterilisation step;

(b) said kinetic implant is loaded with a biologically or pharmaceutically active substance and optionally a stabilising component stabilising the biologically or pharmaceutically active substance, wherein said wall region of said inner, hollow portion is coated with or impregnated with a composition comprising a solvent, a biologically or pharmaceutically active substance and optionally a stabilising component stabilising the biologically or pharmaceutically active substance; and (c) said solvent is removed.

After loading and drying, the kinetic implant is still essentially hollow.

The kinetic implant according to the present invention has also sufficient strength to enable kinetic delivery, in particular transdermal delivery. Other systems known from the prior art are either too weak and have too less weight (e.g. as disclosed by U.S. Pat. No. 6,111,792) to pass the dermis or are too awkward for use in transdermal applications (e.g Biobullets®). The kinetic implant, as determined by testing solid specimen of the kinetic implant (tensile strength testing was performed with test bars 5 mm wide and 2 mm thick made from the biodegradable material on a Zwick testing machine of the type Z 2.5) have a tensile strength of at least about 20 $N/mm^2$ up to about 70 $N/mm^2$. Consequently, there are at least four features which determine the suitability of the kinetic implant according to the present invention in parenteral and in particular in transdermal delivery, i.e. (a) length:diameter ratio, (b) length, (c) weight and (d) strength (tensile and bending).

System for Delivering a Kinetic Implant

The kinetic implant can be delivered to a vertebrate by using devices as for example are disclosed in e.g. U.S. Pat. No. 5,549,560,U.S. Pat. No. 5,989,214 and NL A 9401372,all incorporated by reference. The device according to U.S. Pat. No. 5,549,560 comprises a chamber into which the kinetic implant according to the present invention can be introduced, a barrel connected to the chamber, means for carrying the kinetic implant by means of gas pressure through the barrel into the body of a vertebrate, and means for initiating release of the gas pressure into the barrel. Preferably, the device according to U.S. Pat. No. 5,549,560 is provided with means for blocking the use of the device. The device may also be provided with a magazine comprising a multitude of kinetic implants according to the invention and with means to urge the kinetic implant from the magazine into the chamber. The device according to NL A 9401372 is capable of firing the kinetic implant according to the present invention once only. This device comprises a container comprising a gas under pressure, a chamber suitable for holding a magazine or cartridge comprising a multitude of kinetic implants, a pointed firing pin (e.g. fuse pin, striker, striking pin) which can move as far into the chamber as the position of the container to be fitted, and a duct connecting the locations of the container and the projectile in the chamber.

The firing device must be capable to provide to the kinetic implant a kinetic energy in the range of about 0.1 to about 10 J, preferably about 0.2 to about 5 J (based on a velocity of about 340 m/s).

Accordingly, the present invention provides a system for delivering a kinetic implant according to the present invention to a vertebrate, wherein said system comprises:

(a) a kinetic implant;
(b) optionally a magazine or cartridge for the kinetic implant or for a multitude of kinetic implants; and
(c) a firing device.

The firing device preferably comprises a chamber into which a kinetic implant containing the pharmaceutical preparation can be introduced, a barrel connecting onto this chamber, means for carrying the kinetic implant by means of gas pressure through the barrel into the body for injecting, means for initiating release of the gas pressure into the barrel, and preferably also means for blocking the use of the device when it is not in use. Preferably, the means of generating the gas pressure are formed by a vessel for filling with compressed gas which is connected to the chamber by means of a closing valve. Additionally, it is also preferred that one of the sides of the device comprises a handle-grip and another side of the device comprises the aperture from which the kinetic implant emerges. Preferably, at the end of the barrel a member is arranged, which atomizes a liquid, for instance a disinfecting liquid or a highly coloured liquid onto the skin It is also preferred that in the magazine or cartridge means are arranged for urging the kinetic implants into the chamber.

Alternatively, the firing device comprises a chamber in which the kinetic implant can be transported, a non-penetrating channel connected to the chamber for transporting the kinetic implant into the body, and a fixation means for fixing the end of the channel relative to the skin of the body for injecting in order to prevent a movement of the channel in the direction perpendicularly to the axis of the channel, said fixation means being adapted for clamping engagement to the skin Preferably, the fixation means has chambered protrusions for fixing the end of the channel to the skin of the body, the chambered protrusions extending substantially in the direction of the axis of the channel, wherein the channel is formed by a barrel connecting onto the chamber. This firing device preferably further comprises a discharging means for supplying pressurized gas to the chamber for expelling the kinetic implant through the barrel as well as a spacer element which extends round the mouth of the barrel and which is adapted to direct the air flow preceding the kinetic implant during discharging such that the air flow is guided at least partially along at least that part of the skin of the body for injecting where the kinetic implant subsequently enters the skin Preferably, the spacer element is positioned to hold the mouth of the barrel at a distance from the body for injecting during discharging. It is also preferred that the spacer element has recesses. Additionally, the engaging means are preferably adapted to allow a movement relative to the skin of the vertebrate for injecting when the engaging means are placed at an angle relative to the normal of the skin which is greater than a predetermined angle, the latter being preferably about 30°. It is furthermore preferred that the firing device comprises a safety device for only releasing the discharging means under certain circumstances and that the spacer element is displaced relative to the barrel through a minimum distance in the axial direction of the barrel. The engaging means are adapted to allow a movement relative to the skin of the vertebrate when the engaging means are placed at an angle relative to the normal of the skin which is greater than a predetermined angle and the force with which the spacer element must be depressed to displace the spacer element through the minimum distance can only be generated at an angle smaller than the predetermined angle relative to the normal. Preferably, the firing device comprises a container for pressurized gas, wherein the safety device is adapted to release the discharging means only when the pressure prevailing in the container is greater than a predetermined value. Optionally, the spacer element is connected to an atomizer. The firing device further preferably comprises a safety device, wherein the safety device is connected to transport means for transporting the kinetic implants during discharging of a kinetic implant. These transport means preferably comprise rollers mounted on a system of rods and having grooves wherein the form of the grooves corresponds with the form of the kinetic implant. Suitably, the rollers are driven by a worm wheel.

According to another embodiment, the firing device comprises a container for compressed gas, designed for firing a kinetic implant. This measure results in such a simple construction that the fabrication costs are minimal, specifically so minimal that the costs per firing of the kinetic implant are very low. Moreover, dispensing with a magazine or cartridge suitable for a large number of kinetic implants keeps the mass of the firing device low. This firing device further comprises a chamber suitable for holding a carrier, a pointed firing pin (fuse pin, striker, striking pin) which can move as far into the chamber as the position of the container to be fitted, and a duct connecting the locations of the container and the projectile in the chamber.

EXAMPLES

Example 1

Opened starch in granulated form was made according to the following recipe. A chemically non-modified starch (potato starch purchased from Cerestar, molecular weight about $100 \times 10^6$ Dalton) comprising about 14 wt. % of water, based on the total weight of the chemically non-modified starch, was subjected to extrusion in the presence of 0.5% by weight of lecithin (based on the total weight of the chemically non-modified starch and plasticizer) and a plasticizer (water) at an extrusion temperature of 105° and an extrusion pressure of 14 MPa. The total residence time in the heating zones of the extruder was about 150 s. The strands of opened starch leaving the barrel of the extruder were cut to form a granulate. The amount of plasticizer added was 19.5 wt. %, based on the total weight of chemically non-modified starch and the plasticizer. The water content is determined by using a OHaus apparatus, type MB 45 (conditions: 8 min., 105° C.).

A test specimen made by injection moulding of the opened starch (moisture content 16.5 wt. %) was subjected to the following pre-treatment. The test specimen was first plasticised, where after the test specimen was subsequently treated with enzymes to hydrolyse $\alpha 1 \rightarrow 6$ glucose bonds and dissolved in DMSO. The solution contained the amylose and the residue consisted for the major part of amylopectine. The solution were analysed by using GPC-MALLS-RI (references were standard pullulan samples) for determining amylose content, $M_n$, $M_w$ and MWD (cf. Table 1). Injection moulding conditions were: temperature of 190° C., pressure of 140 MPa, residence time 300 seconds.

TABLE 1

| $M_n$ (kg/mol) | $M_w$ (kg/mol) | MWD | Amylose content (wt. %) |
|---|---|---|---|
| 91 | 115 | 1.27 | 13.3 |

Tensile strength testing of the opened starch was performed by making tensile bars 5 mm wide and 2 mm thick, and using a Zwick Z 2.5 apparatus. The tensile strength was 50.5 N/mm².

A kinetic implant according to the method disclosed in EP A 774.975 was made from the opened starch and was visually inspected by using a standard polarised light stereomicroscope. The number of tension fields were counted and normalised to about 10 mm² of the kinetic implant. The number of tension fields was 24/10 mm². A kinetic implant was also made according to the same method from substantially fully destructurised starch as disclosed in EP A 774.975. Upon visual inspection no tension fields were detected indicating a poor biodegradability.

Example 2

Solid rods were made of opened starch and of the substantially fully destructurised starch as made according to EP A 774.975 and were subjected to a water absorbance test. The solid rods were charged into a beaker and immersed in deionised water. After 10 minutes, the total weight of the rods was determined. The data are shown in Table 2.

TABLE 2

| Material used for making solid rod | Weight (dry) [mg] | Weight (after 10 min.) [mg] | Weight increase (%) |
|---|---|---|---|
| Opened starch | 34.8 | 207.4 | 496 |
| Substantially fully destructurised starch | 33.7 | 42.2 | 25 |

Weight increase was calculated as follows:

100%*{[Weight(after 10 min.)−Weight(dry)]/Weight (dry)}

This example demonstrates that opened starch absorbs water far more rapidly and in much higher amounts when compared to substantially fully destructurised starch according to EP A 774.495. Consequently, upon contact with bodily fluids containing hydrolysing enzymes, opened starch will be degraded much faster than the substantially fully destructurised starch according to EP A 774.495.

Example 3

Two solid test specimen (specimen A was made by injection moulding of fully destructurised starch and had a weight of 67.7 mg and a diameter of 1.4 mm; specimen B was made by injection moulding of opened starch and had a weight of 68.5 mg and a diameter of 1.4 mm) were immersed in a vial in 2 ml of a solution containing 2000 IU/ml of α-amylase. This enzyme is only capable of disrupting 1,4-glycosidic bonds. The injection moulding conditions were: temperature of 190° C., pressure of 140 MPa, residence time 300 seconds. The vials were placed in an oven (temperature 37° C.) for 2 h. Subsequently, the vials were removed from the oven, the supernatant was removed and the residue in each vial was dried during 18 minutes at 105° C. The weight of the dried residue of specimen A was 46.3 mg (about 68% of the original weight) whereas the weight of the dried residue of specimen A was 2.1 mg (about 3% of the original weight). Consequently, specimen B was almost completely degraded within 2 h whereas specimen A was degraded for only about 33%. This example also demonstrated that de degradability can be tuned by varying the ratios of opened starch and fully destructurised starch.

Example 4

Solid rods having a length:diameter ratio of about 12 were made from destructurised starch according to EP A 774.975. Prior to the test they were sterilised and degassed over 48 h. Two steam-sterilised glasses of 250 ml were filled with 99 ml of sterile 50 mM phosphate buffered saline (pH 7.5, 0.1 sodium azide). To glass A, a quantity of 1 ml amylase solution (33 U/ml) and to glass B, a quantity of 1 ml 50 mM 50 mM phosphate buffered saline (pH 7.5, 0.1 sodium azide) was added. Before the start of the experiment, an aliquot of 1 ml was taken from both glasses A and B and stored at −80° C. During the test, the sterilised rods were added to glasses A and B and aliquots were collected at regular intervals. The content of amylose in the aliquots was determined by mixing 50 μl of the aliquot with 100 μl demineralised water and 50 μl 2% lugol, followed by photometric determination of the amount of amylase. The results are shown in Table 3, wherein the concentrations are expressed as absorbance values.

In glass A no increase of amylose content is observed, which supports the conclusion that upon the addition of amylase all amylose is degraded at once as soon as the amylose dissolves. In glass B, however, a gradual increase of amylose is observed which can only be due to the gradual dissolution of amylose. Since the contents of glass A mimic the physiological conditions of bodily fluids containing hydrolysing enzymes in a vertebrate, this experiment demonstrates that kinetic implants made of destructurised starch according to EP A 774.975 are less suitable for implantation purposes and a rapid release of a biologically or pharmaceutically active agent.

After the test, the test samples were filtered and the residues isolated and dried. The difference between the initial weight of the rod and the weight of the residue is indicative of the amount of degradation. It appeared that in glass A about 50% of the rod was dissolved whereas in glass B this was only about 8%. This in vitro experiment demonstrates that even after 192 h (8 days) still 50% of the rod is detectable. Moreover, in an in vivo experiment wherein solid rods (length about 5 cm, diameter about 4.5 mm, ratio length:diameter about 11) were inserted subcutaneously into a bovine animal it appeared that residual material of the solid rods was still detectable after three weeks.

TABLE 3

| Time (h) | A | B |
| --- | --- | --- |
| 0.00 | 0.024 | 0.025 |
| 0.25 | 0.029 | 0.069 |
| 0.50 | 0.031 | 0.148 |
| 0.75 | 0.043 | 0.166 |
| 1.00 | 0.035 | 0.236 |
| 1.50 | 0.028 | 0.270 |
| 2.50 | 0.083 | 0.320 |
| 4.50 | 0.028 | 0.424 |
| 8.00 | 0.031 | 0.502 |
| 10.50 | 0.088 | 0.522 |
| 22.50 | 0.053 | 0.587 |
| 30.00 | 0.043 | 0.595 |
| 72.00 | 0.043 | 0.560 |
| 120.00 | 0.053 | 0.675 |
| 192.00 | 0.055 | 0.730 |

Example 5

A hollow kinetic implant was made from the opened starch according to the present invention, wherein the kinetic implant had a length:diameter ratio of about 12 (length was about 25 mm and the diameter was about 2 mm) and a weight of about 100 mg. The wall thickness was about 100 μm. The hollow kinetic implant was sterilised, filled with an aqueous solution of an antigen and subsequently freeze-dried to remove the water. The hollow kinetic implant was kinetically administered to the neck of pigs from a distance of about 5 mm from the skin. Serum conversion determination established that antibodies were formed thereby demonstrating that the antigen was released.

Example 6

Unloaded, hollow kinetic implants made from opened starch and substantially fully destructurised starch, respectively, were administered subcutaneously in a pig. The hollow kinetic implants made of opened starch were completely degraded within approximately 30 minutes whereas parts, in particular the conical tip, of the hollow kinetic implants made of substantially destructurised starch were could still be detected after 2 hours. This experiment demonstrates that kinetic implants made of opened starch are much faster degraded in vivo than kinetic implants made of substantially fully destructurised starch.

Example 7

The thermostability of kinetic implants loaded with an antigen was tested in the absence and in the presence of trehalose for a period of three weeks. Empty kinetic implants were loaded with an aqueous solution containing the antigen and optionally the stabilising agent and were subsequently subjected to freeze drying. The data are summarised in Table 4.

These data demonstrate that the kinetic implant itself protects the antigen from thermal destruction. A better protection is achieved when the kinetic implant contains trehalose as stabilizing agent.

TABLE 4

| Storage at temperature T (° C.) | Formulation | with/without trehalose (indicated by "+" or "−") | Percentage remaining antigen after 3 weeks |
| --- | --- | --- | --- |
| 4° C. | Solution | − | 97% |
|  |  | + | 94% |
|  | Kinetic implant | − | 100% |
|  |  | + | 100% |
| 37° C. | Solution | − | 82% |
|  |  | + | 91% |
|  | Kinetic implant | − | 73% |
|  |  | + | 100% |
| 60° C. | Solution | − | 0% |
|  |  | + | 0% |
|  | Kinetic implant | − | 18% |
|  |  | + | 67% |

Example 8

Kinetic implants according to Example 7 were also subjected to a long term storage test at 4° C. The results show the amount of antigen remaining after 1 year of storage at 4° C. (cf. Table 5).

These data demonstrate that the antigen in the kinetic implants maintains a higher activity than the antigen kept in solution. A better storage stability is achieved in the presence of trehalose as the stabilizing agent.

TABLE 5

| Original solution day 1 | 100% |
| --- | --- |
| After 1 year storage at 4° C. | Percentage remaining antigen |
| Original solution | 71% |
| Standard freeze dried | 57% |
| Kinetic implant (opened starch), without trehalose | 91% |
| Kinetic implant (opened starch), with trehalose | 100% |

Example 9

This example demonstrates the effectiveness of kinetic implants as antigen delivery vehicle. A hollow kinetic implant, loaded with a commercially available antigen at the inner wall and implanted subcutaneously, induced a similar seroconversion as when the commercial antigen was injected intramuscularly. This demonstrates that kinetic implants according to the invention are an effective antigen delivery system.

Example 10

Opened starch in granulated form was made according to the following recipe. A chemically non-modified starch (potato starch purchased from Cerestar, molecular weight about $100\times10^6$ Dalton) comprising about 14 wt. % of water, based on the total weight of the chemically non-modified starch, was subjected to extrusion in the presence of 0.5% by weight of lecithin (based on the total weight of the chemically non-modified starch and plasticizer) and a plasticizer (water) at an extrusion temperature of 105° and an extrusion pressure of 14 MPa. The total residence time in the heating zones of the extruder was about 150 s. The strands of opened starch leaving the barrel of the extruder were cut to form a granulate. The amount of plasticizer (water) added was 19.5 wt. %, based on the total weight of chemically non-modified starch and the plasticizer. The water content is determined by using a OHaus apparatus, type MB 45 (conditions: 8 min., 105° C.).

Tensile strength testing of the opened starch was performed by making tensile bars 5 mm wide and 2 mm thick, and using a Zwick Z 2.5. The results (averages of five measurements) are summarised in Table 6. The pressure during extrusion was 70 bar (7 MPa). The tensile bars were also visually inspected by using a standard polarised light stereomicroscope. The number of tension fields was counted.

TABLE 6

| Sample No. | Moisture Content (%. wt) | T (° C.) | Residence time (s) | Tensile strength $N/mm^2$ | Number of tension fields/3.2 $cm^2$ |
|---|---|---|---|---|---|
| 19. | 13 | 160 | 80 | 53.1 | 123 |
| 20. | 13 | 160 | 160 | 51.4 | 120 |
| 21. | 13 | 160 | 300 | 53.8 | 105 |
| 22. | 13 | 190 | 80 | 57.7 | 50 |
| 23. | 13 | 190 | 160 | 58.2 | 24 |
| 24. | 13 | 190 | 300 | 56.9 | 10 |
| 25. | 15 | 160 | 80 | 48.5 | 105 |
| 26. | 15 | 160 | 300 | 51.1 | 65 |
| 27. | 15 | 190 | 80 | 55.1 | 24 |
| 28. | 19.5 | 160 | 80 | 51.5 | 58 |
| 29. | 19.5 | 175 | 160 | 53.5 | 14 |

The data of Table 6 show that longer residence time slightly increases tensile strength and reduces the number of tension fields. These data also show that higher temperatures result in a higher tensile strength but a lower number of tension fields.

Further tests (cf. Table 7) show that longer residence times and higher temperatures reduce the number of tension fields.

TABLE 7

| Sample No. | Moisture Content (% . wt) | T (° C.) | Residence time (s) | Number of tension fields in tensile bars |
|---|---|---|---|---|
| 30. | 15 | 160 | 80 | 105 |
| 31. | 15 | 160 | 160 | 75 |
| 32. | 15 | 160 | 300 | 65 |
| 33. | 15 | 190 | 80 | 24 |
| 34. | 15 | 190 | 160 | 20 |
| 35. | 15 | 190 | 300 | 0 |
| 36. | 19.5 | 160 | 80 | 58 |
| 37. | 19.5 | 160 | 160 | 40 |
| 38. | 19.5 | 160 | 300 | 25 |
| 39. | 19.5 | 190 | 80 | 10 |
| 40. | 19.5 | 190 | 160 | 10 |
| 41. | 19.5 | 190 | 300 | 10 |

The invention claimed is:

1. A kinetic implant comprising:

(a) a biodegradable material having a bulk density of 1.0 to 1.5 $kg/dm^3$ and a tensile strength of at least 20 $N/mm^2$ consisting of starch having at least 2 tension fields/3.2 $cm^2$, and, optionally, water;

(b) a biologically or pharmaceutically active substance; and (c) a stabilizing component stabilizing the biologically or pharmaceutically active substance, wherein the stabilizing component is a polyol.

2. The kinetic implant according to claim 1, wherein the starch has a water content of 10 to 25 wt. %, based on the total weight of the starch.

3. The kinetic implant according to claim 1, wherein the starch is obtained by:

(a) extruding a chemically non-modified starch consisting of 15 wt. % to 50 wt. % water, based on the total weight of the chemically non-modified starch, in the presence of a plasticizer, at a temperature of about 30° to about 150° C. and a pressure of about 4.5 to about 25 MPa to form a granulate, wherein the plasticizer is water in an amount ranging from about 20 wt. % to about 50 wt. %, based on the total weight of chemically non-modified starch and the plasticizer; and (b) optionally annealing or conditioning the granulate to form the starch, wherein the starch comprises 13 wt. % to 19.5 wt. % water.

4. The kinetic implant according to claim 3, wherein the granulate is annealed or conditioned for a period of about 0.2 h to about 48 h.

5. The kinetic implant according to claim 3, wherein the chemically non-modified starch has a weight average molecular weight of greater than 20,000,000 g/mol.

6. The kinetic implant according to claim 1, wherein the polyol is a carbohydrate.

7. The kinetic implant according to claim 6, wherein the carbohydrate is a monosaccharide, a disaccharide, a trisaccharide, an oligosaccharide, a polysaccharide, a heteropolysaccharide or a homopolysaccharide.

8. The kinetic implant according to claim 1, wherein the kinetic implant has a length:diameter ratio of more than 4, provided that the length of the kinetic implant is between 1 mm to 50 mm.

9. The kinetic implant according to claim 1, wherein the biologically or pharmaceutically active substance and/or the stabilizing component are homogeneously dispersed within the biodegradable material.

10. The kinetic implant according to claim 1, wherein the kinetic implant comprises an inner, hollow portion, which comprises the biologically or pharmaceutically active substance and the stabilizing component.

11. The kinetic implant according to claim 10, wherein the kinetic implant has an average wall thickness of 10 μm to 2500 μm.

12. The kinetic implant according to claim 10, wherein wall portions of the inner, hollow portion of the kinetic implant are impregnated with the biologically or pharmaceutically active substance and the stabilizing component.

13. The kinetic implant according to claim 10, wherein interior wall portions of the inner, hollow wall portions of the kinetic implant are coated with the biologically or pharmaceutically active substance and the stabilizing component.

14. The kinetic implant according to claim 1, wherein the kinetic implant has a weight such that it can be provided with an amount of kinetic energy in the range of 0.1 to 10 J.

15. The kinetic implant according to claim 14, wherein the kinetic implant has a weight of 1 to 180 mg.

16. The kinetic implant according to claim 1, wherein the kinetic implant, having a width of about 5 mm wide and a thickness of about 2 mm thick, has a tensile strength of 20 $N/mm^2$ to 70 $N/mm^2$.

17. A method for manufacturing a kinetic implant comprising subjecting a biodegradable material having a bulk density of 1.0 to 1.5 $kg/dm^3$ and a tensile strength of at least 20 $N/mm^2$ consisting of starch having at least 2 tension fields/3.2 $cm^2$, and, optionally, water, to injection moulding at a pressure of about 500 to about 3000 bar (about 50 to about 300MPa) and a temperature of about 100° to about 200° C. with residence times of about 5 seconds to about 300 seconds.

18. The method according to claim 17, wherein the kinetic implant has an inner, hollow portion.

19. The method according to claim 18, wherein the kinetic implant has a length:diameter ratio of more than 4, provided that the length of the kinetic implant is between 1 mm to 50 mm.

20. The method according to claim 18, wherein the kinetic implant has an average wall thickness of 10 μm to 2500 μm.

21. The method according to claim 17, comprising sterilizing the kinetic implant.

22. The method according to claim 17, comprising loading the kinetic implant with a composition comprising a biologically or pharmaceutically active substance and optionally with a stabilizing component stabilizing the biologically or pharmaceutically active substance.

23. The method according to claim 18, comprising loading the kinetic implant with a composition comprising a biologically or pharmaceutically active substance and optionally with a stabilizing component stabilizing the biologically or pharmaceutically active substance.

24. A method for administering a biologically or pharmaceutically active substance to a subject in need thereof, comprising delivering parentally to the subject a kinetic implant according to claim 1.

25. The method according to claim 24, wherein the kinetic implant is delivered intramuscularly, subcutaneously or transdermally.

26. The method according to claim 25, wherein the kinetic implant is delivered with a velocity such that the kinetic implant has a kinetic energy of about 0.1 to about 5 J.

* * * * *